United States Patent [19]

Slaugh et al.

[11] Patent Number: 4,946,560
[45] Date of Patent: * Aug. 7, 1990

[54] PROCESS FOR SEPARATING ALPHA AND INTERNAL OLEFINS

[75] Inventors: Lynn H. Slaugh, Cypress; Howard L. Fong, Sugarland, both of Tex.

[73] Assignee: Shell Oil Company, Houston, Tex.

[*] Notice: The portion of the term of this patent subsequent to Apr. 10, 2007 has been disclaimed.

[21] Appl. No.: 263,218

[22] Filed: Oct. 27, 1988

[51] Int. Cl.$^5$ .................... B01D 3/34; C07C 7/152
[52] U.S. Cl. .................... 203/38; 203/80; 203/88; 203/91; 585/809; 585/814; 585/864; 585/867
[58] Field of Search .............. 203/38, 29, 69, 30, 203/57, 80, 47, 48, DIG. 6; 585/664, 809, 812, 814, 816, 867, 864

[56] References Cited

U.S. PATENT DOCUMENTS

| | | | |
|---|---|---|---|
| 3,052,737 | 9/1962 | Slaugh | 585/251 |
| 3,306,946 | 2/1967 | Snyder et al. | 585/809 |
| 3,534,116 | 10/1970 | Fuller | 585/867 |
| 3,864,420 | 2/1975 | Dombro | 585/664 |
| 4,710,273 | 12/1987 | Okamoto | 203/38 |

FOREIGN PATENT DOCUMENTS 833939  5/1981  U.S.S.R. ............. 585/809

*Primary Examiner*—Wilbur Bascomb

[57] ABSTRACT

A feedstock containing alpha olefins and internal olefins is converted into a first product having an enhanced internal olefin content over that of the feedstock and into a second product having an enhanced alpha olefin content over that of the feedstock by:

(a) contacting the feedstock with an anthracene at a temperature ranging from 150° to 275° C. to form an olefin adduct with anthracene,
(b) separating the adduct from the product of step (a) to leave a first product enriched in internal olefin,
(c) heating the separated adduct at a temperature of from 250°–400° C. to produce anthracene and an olefin product enriched in alpha olefin, and
(d) separating anthracene from the product of step (c) to produce a second product enriched in alpha olefin. Linear olefins are preferred feedstocks.

12 Claims, No Drawings

PROCESS FOR SEPARATING ALPHA AND INTERNAL OLEFINS

Field of the Invention

This invention relates to a process for separating alpha olefins and internal olefins from a mixture comprising alpha olefins and internal olefins.

Background of the Invention

Many industrial processes produce olefins that are mixtures of alpha olefins and internal olefins. Due to the similarities in properties of alpha and internal olefins of the same molecular weight it is not an easy matter to separate the two. Olefins are frequently used as intermediates for the production of oil additives and detergents. The alpha and internal olefins can each be used to prepare end products having very different properties although the olefins utilized have the same molecular weight. Alpha olefins are particularly valued, although the internal olefins have particular specialized uses such as gasoline additives. A process that would separate a mixed linear olefin feedstock into component alpha and internal olefins would be of considerable value.

Copending application Ser. No. 07/263,225, filed Oct. 27, 1988 discloses the use of an isomerization catalyst coupled with an anthracene to convert an internal olefin feedstock or a mixed alpha and internal olefin feedstock to a product having an enhanced alpha olefin content.

U.S. Pat. No. 3,052,737, issued Sept. 4, 1962, discloses reacting anthracene with vinylcyclohexene to produce an adduct which is then hydrogenated to convert the cyclohexene ring to a cyclohexane ring, followed by pyrolysis to produce vinylcyclohexane and anthracene. This reference does not suggest that anthracene would be useful in separating alpha and internal linear olefins.

Summary of the Invention

This invention relates to a process for converting a feedstock comprising alpha olefins and internal olefins into a first product wherein the internal olefin content is enriched or enhanced over that of the feedstock and a second product wherein the alpha olefin content is enriched or enhanced over that of the feedstock which process comprises:

(a) contacting said feedstock with an anthracene at a temperature ranging of from about 150° to about 275° C. to form an olefin adduct with anthracene, (b) separating said adduct from the product of step (a) to leave said first product enriched in internal olefin, (c) heating said separated adduct at a temperature of from between about 250° to about 400° C. to produce anthracene and an olefin product enriched in alpha olefin, and (d) separating anthracene from the product of step (c) to produce said second product enriched in alpha olefin. Linear olefins are a preferred feedstock.

Detailed Description of the Invention

The feedstock olefins preferably used in the process of the instant invention are those olefins that are produced by commercial processes such as the oligomerization of ethylene, followed by isomerization and disproportionation. These feedstocks are typically substantially linear olefins. Small amounts of branched olefins may be present in such feeds and do not detract from the process of the instant invention. These branched olefins will tend to be separated in the same fashion as the linear olefins, the degree of separation being determined by the degree and location of the branching. Typically the feed olefins will have a carbon number ranging from about 6 to about 22, more preferably from about 8 to about 18. The physical properties of the olefins determine the suitable carbon numbers to be utilized. At the reaction temperature the olefins to be separated should be in the liquid or gaseous state rather than in the solid state. Olefins with carbon numbers greater than 18 and lower than 6 can be utilized in the instant process but from a commercially practical point of view feedstocks with carbon number ranging from about 6 to about 18 will be most frequently used.

Anthracene is utilized in the instant process to form the adduct primarily with the alpha olefin in the feedstock. As used herein "anthracene" refers to $C_{14}H_{10}$ (molecular weight 178.15) as well as substituted anthracenes possessing similar adducting properties as the unsubstituted anthracene including but no limited to anthracene bearing one, two or more simple substituents, including but not limited to, lower alkyl, e.g., methyl, ethyl, butyl; halo, e.g., chloro, bromo, fluoro; nitro; sulfato; sulfonyloxy; carboxyl; carbo -lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituents utilized should be inert under the reaction conditions and relatively small, such that they do not provide so much steric hinderance that the Diels-Alder reaction is inhibited. For example, 9-phenylanthracene is useful, whereas 9,10-phenylanthracene inhibits the Diels-Alder reaction. Suitable substituted anthracenes can be determined by routine experimentation.

The process of the instant invention is basically a three step process wherein (a) anthracene is reacted with the olefin to form an adduct, (b) the adduct is separated from the reaction mixture and (c) the adduct is pyrolized to release the olefin and regenerate the anthracene.

The Diels-Alder adduct forming reaction is carried out in a conventional fashion. It may be carried out continuously in a stirred tank reactor wherein olefin and anthracene are added continuously to a stirred tank and a reaction product is continuous withdrawn from the stirred tank. Alternatively, the reaction may be carried out in a batch reactor, wherein the olefin and the anthracene are charged to an autoclave which is then heated to reaction temperature to complete the reaction. The reaction is typically carried out over a range of temperatures from about 150° to about 275° C., preferably from about 200° to about 250° C., and most preferably from about 210° to about 240° C. Pressures are not critical and typically run from about atomspheric to about 100 atmospheres. The reaction can be carried out in the gas phase or liquid phase or mixed gas-liquid phase, depending on the volatility of the feed olefins.

Stoichiometric proportions or an excess of either olefin or anthracene can be used in forming the adducts but an excess of olefin is preferred. Advantageous ratios of about 1 to 2 moles of the olefin to the anthracene are preferred.

An inert solvent can be utilized to dissolve the feed olefins or the anthracene or both in the reactor. Preferred solvents are the hydrocarbon solvents which are liquid at reaction temperatures and in which the olefins, anthracence and olefin-anthracene adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

After the anthracene-olefin adduct has been formed, it is separated from the reaction mixture. The olefin-anthracene adduct is separated from the reaction mixture by conventional means. For example, it may be separated by flash distillation of the olefin to leave the adduct. Preferably, it is separated by cooling the reaction mixture until the adduct crystallizes out, followed by filtration or centrifugation to remove the unreacted olefin. In most cases the unreacted anthracene will separate out with the adduct.

After the adduct has been separated from the reaction mixture there is left a first product that is enriched in internal olefins over that of the feedstock olefins. This first reaction product may be subjected to one or more additional reactions with anthracene followed by separation of the adduct to further enhance the internal olefin content of the first product.

The final step of the instant process is to heat or pyrolyze the recovered olefin-anthracene adduct at a temperature of from about 250° to about 400° C. preferably from about 300° to about 350° C. This pyrolysis frees the olefin from the anthracene. The anthracene is then separated from the resulting mixture to produce a second product enriched in alpha olefin content over that of the olefin feedstock. This separation is carried out by conventional means, e.g., flash distillation, filtration, centrifugation, etc. This second reaction product may be subjected to one or more additional reactions with anthracene followed by separation of the adduct and pyrolysis of the olefin-anthracene adduct to produce a product having an even more enhanced alpha olefin content.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The present invention will now be illustrated by means of the following illustrative embodiments and examples which are provided for illustration and are not to be construed as limiting the invention.

Examples

The following example illustrates the process the instant invention.

A 100 ml. Parr autoclave was charged with 0.054 moles of anthracene (unsubstituted) and purged three times with argon and sealed. The autoclave was placed in a dry box and 0.212 moles of decene feed which had been nitrogen purged was added to the autoclave along with 20 ml. of dry, nitrogen purged toluene. The autoclave was sealed, removed from the dry box, placed in a heating bath and heated to 220°–230° C. for 24 hours. The autoclave was stirred at 600 rpm during heating. The autoclave was then cooled to 20° C. The precipitated anthracene and dodecene-anthracene adduct was filtered out of the reaction product. The solid anthracene and dodecene-anthracene adduct were pyrolyzed in a nitrogen flow-pot heated to 300°–350° C. for 0.5 hours. After pyrolysis, the reaction product was filtered to separate the anthracene from a dodecene oil product. This product was analyzed by gas chromatography and ozonolysis. The results are shown in Table 1.

Additional experiments were carried out using various substituted anthracenes. The results of these experiments are shown in Table 1.

TABLE 1

| Example | Anthracene Used for Diels-Alder Adduct Formation | Temp. of Adduct Formation °C. | RXN Time Hrs | Decene Composition of Feeds and Products of Adduct Pyrolysis | | | | |
|---|---|---|---|---|---|---|---|---|
| | | | | 1-Decene | 2-Decene | 3-Decene | 4-Decene | 5-Decene |
| | (N-decene feed) | — | — | 53.2 | 19.6 | 12.4 | 10.4 | 4.4 |
| 1 | Anthracene | 220–230 | 24 | 84.8 | 8.3 | 4.0 | 2.3 | 0.8 |
| 2 | 9,10-dichloroanthracene | 220–230 | 24 | 77.0 | 14.8 | 4.7 | 2.7 | 0.8 |
| 3 | 9,10-dimethylanthracene | 220–230 | 24 | 93.8 | 5.1 | 0.7 | 0.3 | 0.1 |
| 4 | 9,10-diphenylanthracene | 220–230 | 24 | No Reaction | | | | |
| 5 | 9-methylanthracene | 220–230 | 24 | 88.1 | 7.7 | 2.5 | 1.2 | 0.5 |
| 6 | 9-phenylanthracene | 220–230 | 24 | 69.3 | 15.8 | 7.6 | 5.6 | 1.7 |
| 7 | 2-t-butylanthracene | 220–230 | 24 | 85.0 | 8.1 | 3.7 | 2.4 | 0.8 |

We claim:

1. A process for converting a feedstock comprising alpha olefins and internal olefins into a first product wherein the internal olefin content is enriched over that of the feedstock and a second product wherein the alpha olefin content is enriched over that of the feedstock which process comprises:
   (a) contacting said feedstock with an anthracene at a temperature ranging of from about 150° to about 275° C. to form an olefin adduct with anthracene,
   (b) separating said adduct from the feedstock to leave said first product enriched in internal olefin,
   (c) heating said separated adduct at a temperature of from between about 250° to about 400° C. to produce anthracene and an olefin product enriched in alpha olefin, and
   (d) separating anthracene from the product of step (c) to produce said second product enriched in alpha olefin.

2. The process of claim 1 wherein step (a) is carried out at a temperature of from about 200° to about 250° C.

3. The process of claim 2 wherein step (a) is carried out at a temperature of from about 210° to about 240° C.

4. The process of claim 2 wherein step (c) is carried out at a temperature of from about 300° to about 350° C.

5. The process of claim 3 wherein step (c) is carried out at a temperature of from about 300° to about 350° C.

6. The process of any one of claims 1 to 5 wherein the separations carried out in steps (b) and (d) are carried out by vacuum distillation.

7. The process of any one of claims 1 to 5 wherein the separations carried out in steps (b) and (d) ar carried out by first cooling followed by filtration or centrifugation.

8. The process of any one of claims 1 to 5 wherein the feedstock olefins have carbon numbers ranging from about 6 to about 22.

9. The process of claim 8 wherein the feedstock olefins have carbon numbers ranging from about 8 to about 18.

10. The process of any one of claims 1 to 5 wherein the feedstock olefins comprise linear olefins.

11. The process of claim 8 wherein the feedstock olefins comprise linear olefins.

12. The process of claim 9 wherein the feedsock olefins comprise linear olefins.

* * * * *